United States Patent
Shepherd et al.

(10) Patent No.: US 10,758,601 B2
(45) Date of Patent: Sep. 1, 2020

(54) EIMERIA VACCINE WITH IMPROVED EFFICACY

(71) Applicant: Intervet Inc., Madison, NJ (US)

(72) Inventors: Alex Shepherd, Northampton (GB); Colin Crouch, High Wycombe (GB)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 16/471,057

(22) PCT Filed: Dec. 21, 2017

(86) PCT No.: PCT/EP2017/084000
§ 371 (c)(1),
(2) Date: Jun. 19, 2019

(87) PCT Pub. No.: WO2018/115229
PCT Pub. Date: Jun. 28, 2018

(65) Prior Publication Data
US 2019/0328858 A1    Oct. 31, 2019

(30) Foreign Application Priority Data
Dec. 22, 2016    (EP) .................................... 16206058

(51) Int. Cl.
| | | |
|---|---|---|
| *A61K 39/002* | (2006.01) | |
| *A61K 39/12* | (2006.01) | |
| *A61K 49/00* | (2006.01) | |
| *A61K 39/012* | (2006.01) | |
| *A61P 31/04* | (2006.01) | |
| *A61K 39/00* | (2006.01) | |

(52) U.S. Cl.
CPC ............ *A61K 39/012* (2013.01); *A61P 31/04* (2018.01); *A61K 2039/55561* (2013.01)

(58) Field of Classification Search
CPC ..... A61K 39/00; A61K 39/002; A61K 39/012
USPC ....... 424/9.1, 9.2, 93.1, 184.1, 234.1, 265.1, 424/267.1
See application file for complete search history.

(56) References Cited

FOREIGN PATENT DOCUMENTS

| WO | 2006113594 A1 | 10/2006 |
|---|---|---|
| WO | 2008109083 A2 | 9/2008 |
| WO | 2011011873 A1 | 2/2011 |

OTHER PUBLICATIONS

Ahmad, T.A.. et al., Development of immunization trials against *Eimeria* spp., Trials in Vaccinology, 2016, pp. 38-47, 5.
Cozma, V. and Titilincu, A., Passive immunity in poultry coccidiosis, Scientia Parasitologica, 2007, pp. 97-108, 2-3.
European Search report for 16206058.6 dated Apr. 4, 2017, 12 pages.
International Search Report for appl. PCTEP2017084000, dated Mar. 6, 2018, 5 pages.
Irish Medicines Board: "Summary of Product Characteristics Paracox", https://www.hpra.ie/img/uploaded/swedocuments/LicenseSPC_10996-245-001_29082011165942.pdf, XP055282943, retrieved from Internet Jun. 22, 2016.
Kumar Gupta, S et al., Toll-like receptor-based adjuvants: enhancing the immune response to vaccines against infectious diseases of chicken, Expert Rev. Vaccines, 2014, pp. 909-925, 13(7).
MSD Animal Health GmbH: Paracox 8 ad us. vet., www.vetpharm.uzh.ch/tak/00000000/00001397.VAK, XP055282820, retrieved from Internet Jun. 22, 2016.
Sumners, L.H.et al., Expression of Toll-like receptors and antimicrobial peptides during Eimeria praecox infection in chickens, Experimental Parasitology, 2011, pp. 714-718, 127.

*Primary Examiner* — Rodney P Swartz

(57) ABSTRACT

The present invention relates to the fields of veterinary parasitology and -vaccinology; more specifically the invention relates to a composition comprising live *Eimeria* oocysts and a pharmaceutically acceptable carrier. The composition is characterised in that it comprises a TLR3 agonist. The composition can be used to prepare a vaccine for poultry against Coccidiosis. The vaccine can be applied for example as a coarse spray on day-old chicks. The TLR3 agonist in the vaccine allows for a reduction of the dose of *Eimeria* oocysts up to 4 fold, while obtaining the same level of protection against challenge as from a vaccine without the TLR3 agonist. Alternatively, when employing a conventional dose of *Eimeria* oocysts in the vaccine, the TLR3 agonist causes an earlier onset of immunity, resulting in a significant reduction of the intestinal lesion score upon challenge, already at 2 instead of at 3 weeks after vaccination.

12 Claims, 4 Drawing Sheets

EIMERIA VACCINE WITH IMPROVED EFFICACY

CROSS-REFERENCE TO RELATED APPLICATIONS

Figure 1:
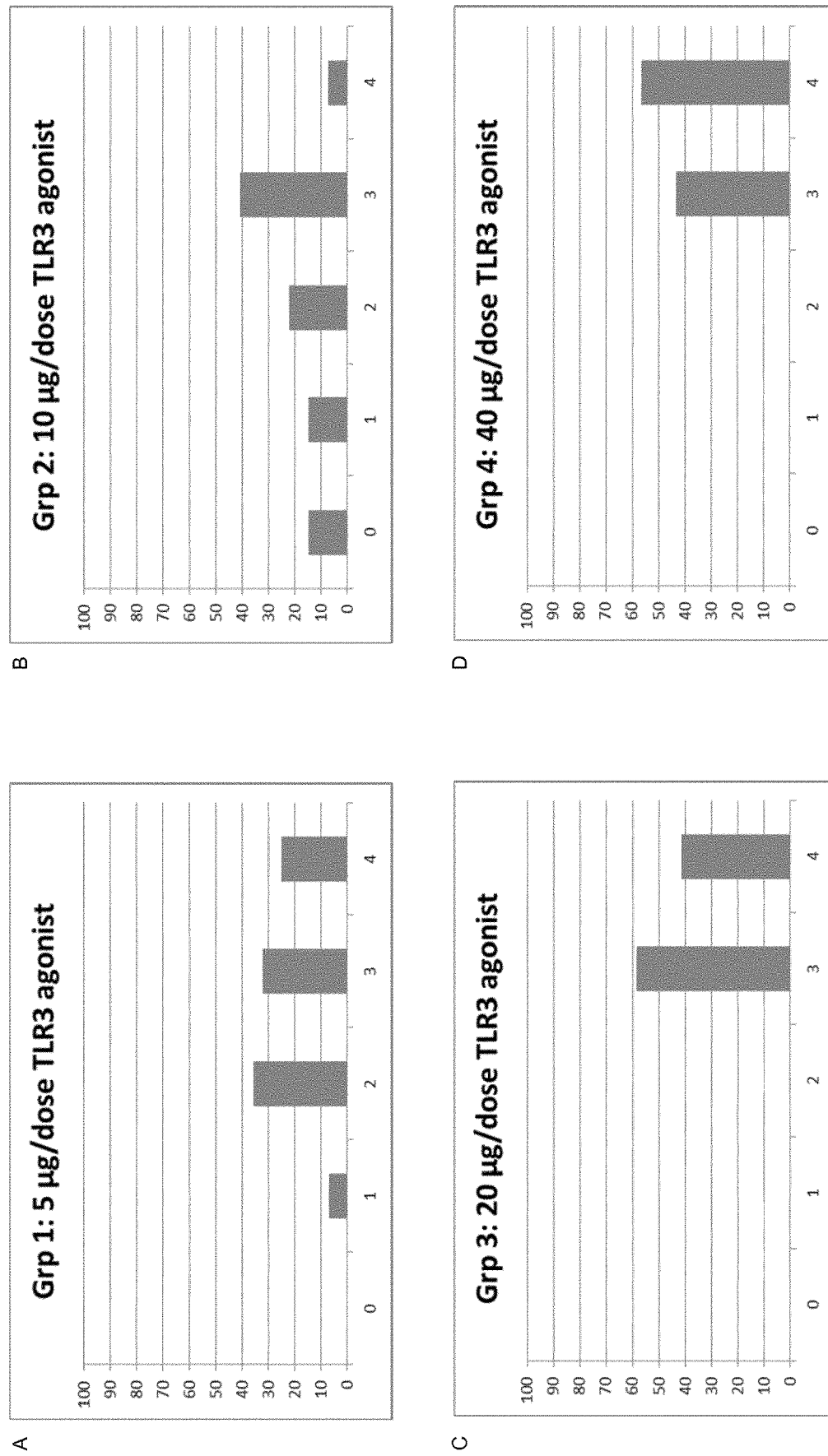
Figure 1:
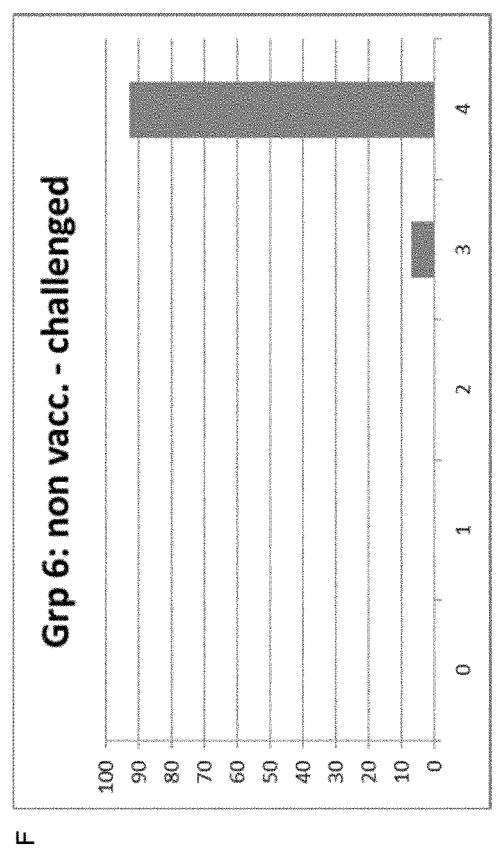
Figure 1:
Figure 1:
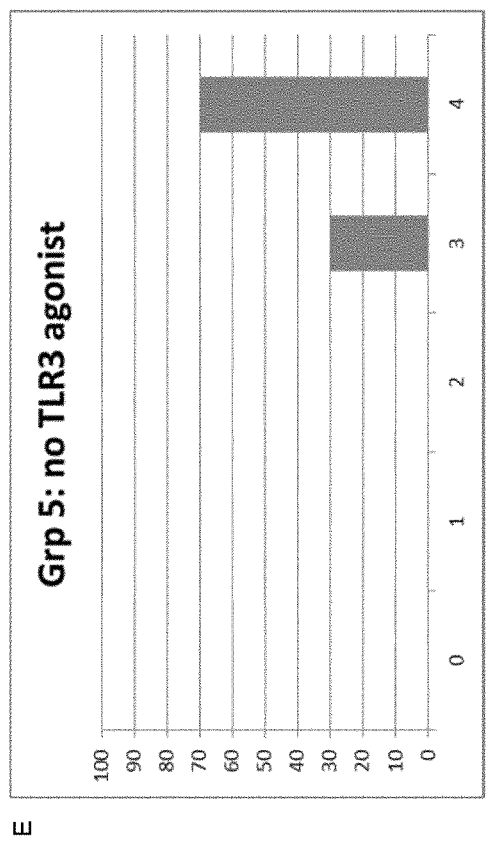
Figure 1:
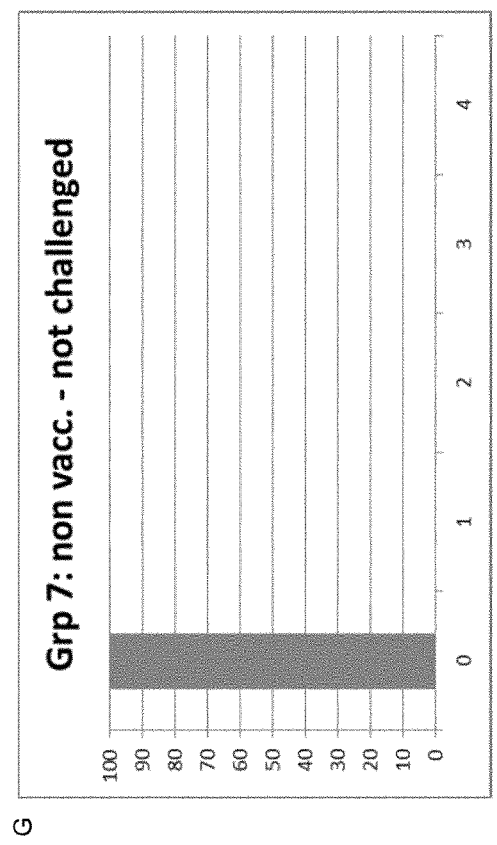

This application is a national stage entry under 35 U.S.C. § 371 of PCT/EP2017/084000, filed on Dec. 21, 2017, which claims priority to EP Application 16206058.6, filed on Dec. 22, 2016, the content of PCT/EP2017/084000 is hereby incorporated by reference in its entirety.

The present invention relates to the fields of veterinary parasitology and -vaccinology; more specifically the invention relates to a composition comprising live *Eimeria* oocysts and a pharmaceutically acceptable carrier, to a method for the preparation of the composition, to medical uses of the composition in a vaccine for poultry against Coccidiosis, and to methods and uses of the vaccine.

*Eimeria* are protozoan parasites of the phylum Apicomplexa, and the class Coccidia, and occur worldwide. When infecting a host, they cause an enteric disease-complex, called: Coccidiosis. *Eimeria* have a complex lifecycle with multiple stages, some developing outside the host. *Eimeria* infection occurs by ingestion of sporulated oocysts and can happen from the first day of age. Next sporozoites are released in the gut, which then colonize a section of the host's intestine, by invading gut epithelial cells. Replication leads to release of merozoite stages, and rupture of gut-epithelial cells from the host. Next the merozoites re-infect further epithelial cells, and this continues for up to another four cycles of 4-6 days. Finally the sexual stages develop, which produce oocysts that are released with the faeces. After sporulation in the environment the cycle starts anew (Shirley et al., 2005, Adv. in Paras., vol. 60, p. 285).

Symptoms of *Eimeria* infection in poultry vary from loss of appetite, to enteritis and bloody diarrhoea, to organ failure due to build-up of necrotic tissue in the intestines, and even mortality. Consequences are a drop in feed conversion rate, reduced growth rate, reduced egg production, and susceptibility to secondary infections; all causing major discomfort to affected birds, and severe economic damage to commercial poultry operations. For an overview of poultry Coccidiosis, see textbooks such as: "The Merck veterinary manual" (10th ed., 2010, C. M. Kahn edt., ISBN: 091191093X), or: Swayne et al., eds.: "Diseases of Poultry", 13th ed., Wiley-Blackwell, Ames, Iowa, USA.

Reduction of *Eimeria* infection and Coccidiosis can be obtained by administering anti-coccidial drugs (coccidiostats) via the feed, but build-up of resistance and presence of drug-residues in animal products are a constant concern. Therefore *Eimeria* infection and associated signs of disease in poultry are preferably combated by vaccination. Because no effective subunit- or recombinant DNA based *Eimeria* vaccines are available, most employed for poultry are live vaccines, comprising sporulated oocysts from one or more species of *Eimeria*. Their natural replication in the bird's intestines induces a strong immunity, by both humoral and cellular routes of the immune system. Full immunity is commonly reached at about 3 weeks post-vaccination. A single live oocyst vaccination at an early age-helped by occasional wild type booster infections later on-is sufficient to protect the birds for their lifetime.

The live vaccine oocysts can be of wild-type or of attenuated pathotype. A special class of attenuated *Eimeria* are the so-called precocious strains. Such attenuated strains produce lower numbers of oocyst output and/or less damage to a vaccinated target's intestine.

The efficacy of an *Eimeria* vaccine is usually determined by assessing the main criteria for infection and disease after a challenge infection with a virulent *Eimeria* strain: gut lesion score, live bodyweight gain, and oocyst output. A paper describing the relevance of these criteria for assessing *Eimeria* vaccine efficacy is: Williams & Catchpole, (2000, Vaccine, vol. 18, p. 1178-1185).

Typically a live avian *Eimeria* vaccine will contain sporulated oocysts from several *Eimeria* species, as immunity is species-specific. Also, different *Eimeria* species infect different species of poultry for example chickens and turkeys. Examples of some commercial Coccidiosis vaccines for poultry are: Coccivac™, Paracox™, or Fortegra™ (all MSD Animal Health); Immucox™ (Ceva); and Inovocox™ (Huvepharma).

Such vaccines are commonly administered by a method of mass vaccination in order to reduce costs, such as by spray on the birds or on the feed, or via the drinking water. Because field infection pressure exists from the first day of age, therefore vaccination is preferably applied to birds as young as possible. This can conveniently be done by spray administration at the hatchery, when chicks have just hatched and are kept in open trays. This route reaches the body of the birds as well as their direct surroundings. The vaccine is then ingested by the birds via oral-, nasal, and/or ocular route by their tendency to peck-up droplets and to preen their feathers. To improve uptake of the sprayed vaccine, its visibility is commonly increased by adding a bright colour.

In European patent-application no. EP 15203012 a gel-based *Eimeria* vaccine is described that can be delivered to birds by way of spraying. The gel has a viscosity of between about 200 and about 4000 mPa·s, which is provided by Xanthan gum. Standard spray vaccination equipment can be used, because of the pseudoplastic properties of Xanthan gum. In this way, gel-beads can be produced of a size that is appealing for pecking up by the birds. This results in an enhanced vaccine-uptake over previous *Eimeria* spray vaccines, and a rapid development of immunity.

The main bottleneck in the commercial and large-scale production of live *Eimeria* oocyst vaccines is the generation of the *Eimeria* oocysts themselves: because it is currently not possible to culture all developmental stages of an *Eimeria* in vitro, therefore *Eimeria* oocysts need to be produced in donor poultry hosts, and be isolated from their faeces. The *Eimeria* oocysts are then purified, sporulated and formulated into a vaccine. In addition, because of the lack of effective cross-protection, up to 14 different *Eimeria* species of veterinary importance may need to be produced by donor birds.

This is such a laborious and burdensome method of vaccine production that so-far commercial production cannot comply with the demand in the market for these vaccines. Consequently, there is a need both from an economical-as well as from an ethical viewpoint, to maximise the effectiveness of such hard-earned live *Eimeria* oocyst vaccines.

Immune responses can be amplified by the use of an adjuvant. This can be a single molecule or a complex composition, and may stimulate a target's immune response in a specific or non-specific manner. Typically adjuvants are applied with inactivated- or subunit vaccines as these are hardly effective without such immune-stimulation, but only rarely with a vaccine of a replicative micro-organism.

Among the many possible adjuvants, immunostimulatory oligodeoxynucleotides are an option. First reports described the use of non-methylated CpG motifs present in bacterial DNA, by Krieg et al. (1995, Nature, vol. 374, p. 546). In the subsequent two decades the underlying mechanism was revealed as a method for sensing of and response to the invasion of a micro-organism, by the recognition of conserved structural motifs, so called pathogen-associated molecular patterns (PAMPs), existing e.g. in the genomic material of invading micro-organisms. For this purpose, the innate immune system employs specific pattern recognition receptors such as Toll-like receptors (TLRs).

TLRs are type I transmembrane glycoproteins, and the binding of an agonistic ligand leads to a cell-signalling cascade resulting in the expression of type 1 interferons and pro-inflammatory cytokines (interleukins and tumour necrosis factor alpha). In addition this is a basis for the stimulation of the secondary, acquired immune response. (Kawai & Akira, 2010, Nature Immunol., vol. 11, p. 373).

In chickens use of TLR agonists has been studied for their ability to act as adjuvant and stimulate immunity against different micro-organisms, mainly viruses (St. Paul et al., 2013, Vet Imm. & Imm. pathol., vol. 152, p. 191-199; Gupta et al., 2014, Expert Rev. Vaccines, vol. 13, p. 909-925). However results are variable at best, and no single TLR agonist stands out favourably.

In mammals as well as in birds, TLR3 is dedicated to the detection of viral replication, by way of sensing an intermediary: double-stranded RNA. This is reviewed in Chen et al. (2013, Vet. Research, vol. 44, p. 82). In practice a synthetic dsRNA, or an analogue, can be applied as a TLR3 agonist, for example a dimeric homopolymer of polyinosinic-polycytidylic acid (poly I:C) or polyadenylic-polyuridylic acid (poly A:U). Both poly I:C and poly A:U have been studied for their effect in a variety of infection models and even in cancer-immunology. For example: EP 344.808 describes a Coccidiosis vaccine of a recombinant Eimeria protein, where poly I:C is mentioned as a potential adjuvant. However its examples use a 65 kDa antigen in Freund's complete adjuvant, or expressed from a Vaccinia virus vector.

WO 2015/042.369 describes an oil-emulsion vaccine which comprises polyI:C and a recombinant antigen of Clostridium perfringens, to protect against Eimeria maxima infection.

The commercial vaccine Evalon™ (Hipra), is a live Eimeria oocyst vaccine for spraying, which is adjuvated with an oily suspension containing the mineral oil Montanide™.

Consequently, there is no description or suggestion in the art on the use of a TLR3 agonist with live Eimeria oocysts.

Sumners et al. (2011, Exp. Parasitol., vol. 127, p. 714-718) investigated change in expression profile of a number of TLRs and anti-microbial peptides in chickens, resulting from an infection with E. praecox. Results found varied and for Ch TLR3 were inconsistent, as this was up-regulated in one experiment, but down-regulated in another where a higher infective dose was used. Sumner suggests to include E. praecox as vaccine component, but makes no suggestion to use any specific factor as adjuvant.

It is therefore an object of the present invention to overcome a disadvantage in the prior art, and to accommodate to a need in the field by providing a more efficacious Eimeria vaccine.

Surprisingly it was found that this object can be met, and consequently one or more disadvantages of the prior art can be overcome, by adding a Xanthan gum and a TLR3 agonist to a composition comprising live Eimeria oocysts. This composition can then be used to prepare a vaccine for poultry against Coccidiosis; the vaccine can be administered by spray, and is then ingested by the poultry.

In the resulting vaccine, the TLR3 agonist can allow for a reduction of the dose of Eimeria oocysts up to 4 fold, while obtaining the same level of protection against challenge as from a vaccine without the TLR3 agonist. Alternatively, when employing a conventional dose of Eimeria oocysts in the vaccine, the TLR3 agonist causes an earlier onset of immunity, resulting in a significant reduction of the intestinal lesion score upon challenge, already at 2 instead of at 3 weeks after vaccination. Both these effects are very significant economically.

This was not at all straightforward, because the inventors were lost for choice when selecting a way to make Eimeria vaccination more efficacious: choosing the addition of an adjuvant was only one option among alternatives such as improvements to the formulation as such, or to the dose, the method, or to the route of administration, etc. Also an adjuvant is not a common ingredient of a live vaccine. Further, when selecting a suitable and effective adjuvant from many possible adjuvants to consider, specifically for use in poultry, PAMPs were not the most promising candidates. And finally, when selecting from possible PAMPs, a TLR agonist is only one of many options, and again, TLR3 is only one of many TLRs to choose from, and certainly not one that stands out for proven efficacy.

The inventors were therefore surprised to find that a TLR3 agonist was so successful for this type of vaccine. For example, there was no information on immune stimulation against a live replicating parasite, and especially no information on the stimulation by a TLR3 agonist of intestinal immunity. This stimulation was found to be effective for a live and replicating Eimeria parasite. Further it was highly unexpected that the TLR3 agonist could at all survive ingestion via the oral route and passage through the intestinal tract.

Although the inventors do not want to be bound by any theory or model that might explain these findings, they speculate that the TLR3 agonist is able to stimulate the intestinal immune-response against the replicating Eimeria. This probably results in an earlier and/or a stronger vaccination response. In the resulting vaccine. The Xanthan gum facilitates the formation of droplets from the vaccine upon spray administration, and upon ingestion of these gel-droplets, the Xanthan gum may be involved in the protection of the TLR3 agonist during the delivery to the intestines.

This also was surprising, because prior studies using TLR3 agonists as adjuvant had shown this could not be administered by oral route. So even when considering to use a TLR3 agonist as vaccine adjuvant, there was no indication if and how this could be delivered to the relevant site of action: the avian gut, in conjunction with an oral vaccine.

In fact, the conditions within the intestinal tract, along with the acidic environment of the stomach, would favor the rapid hydrolysis of any form of RNA. This is only exacerbated by the presence of RNases, both locally, and as secreted or released by the bacteria of the gut microbiome. Any naked RNA or RNA analogue, such as is used in the present invention, is therefore prone to immediate degradation before ever reaching the required site of action. This is also described in Zhou et al. (2007, J. of Immunol., vol. 178, p. 4548-4556), who found that the mucosal injury observed following intraperitoneal administration of dsRNA, resulting from TLR-3 activation, was not observed following oral administration of the dsRNA.

Similarly, Lantier et al. (2014, J. of Inf. Dis., vol. 209, p. 457-467) describe that administration of poly I:C helped to induce protection in mice against *Cryptosporidium parvum*. This however only when administration was by i.p. route, as oral administration failed to show any measurable response.

Both Zhou and Lantier suggest that this effect is due to degradation of the RNA or the analogue. Consequently, the inventors have found a way to deliver immunologically active amounts of a TLR3 agonist to a site of action in the gut of an avian target, while using only relatively low concentrations of the agonist, by incorporating the TLR3 agonist in an oral vaccine comprising Xanthan gum.

The combination with Xanthan gum was thus found to protect an analogue of dsRNA such that it can now be administered by oral route, in relatively low concentrations, and still induce in the avian gut, a detectable clinical improvement on the protective response obtained following oral *Eimeria* vaccination of poultry.

Therefore in one aspect the invention relates to a composition comprising live *Eimeria* oocysts and a pharmaceutically acceptable carrier, characterised in that the composition comprises between about 0.3 and about 5% w/v Xanthan gum and a TLR3 agonist.

The composition according to the invention can be employed to prepare a vaccine for poultry against Coccidiosis. Details and preferences of a Coccidiosis vaccine, its manufacture, and its use will be described herein below.

The term "comprising" (as well as variations such as "comprise", "comprises", and "comprised") as used herein, intends to refer to all elements, and in any possible combination conceivable for the invention, that are covered by or included in the text section, paragraph, claim, etc., in which this term is used, even if such elements or combinations are not explicitly recited; and not to the exclusion of any of such element(s) or combinations.

Therefore any such text section, paragraph, claim, etc., can therefore also relate to one or more embodiment(s) wherein the term "comprising" (or its variants) is replaced by terms such as "consist of", "consisting of", or "consist essentially of".

"oocysts" are well-known micro-organisms that are one of the life-cycle stages of an Apicomplexan parasite such as an *Eimeria*.

The oocysts are "live" when they are capable of initiating an *Eimeria* replicative cycle when under appropriate conditions, such as in the intestines of a bird.

An "*Eimeria*" is well known in the art as a parasite belonging to the Eimeriidae family. These parasites and their induced diseases are described in well-known textbooks (supra). An *Eimeria* displays the characterising features of its taxonomic group-members such as the morphologic, genomic, and biochemical characteristics, as well as the biological characteristics such as physiologic, immunologic, or pathologic behaviour.

As is known in the field, the classification of a micro-organism as a particular "species" is based on a combination of such features. The invention therefore also includes *Eimeria* that are sub-classified therefrom in any way, for instance as a subspecies, strain, isolate, genotype, variant, subtype or subgroup and the like.

The *Eimeria* for the invention can replicate in a species of poultry, and for example comprise the *Eimeria* species: *E. acervulina, E. tenella, E. maxima, E. brunetti, E. mitis, E. mivati, E. necatrix, E. praecox, E. hagani, E. meleagrimitis* (type 1 or type 2), *E. adenoides, E. gallopavonis, E. dispersa, E. innocua, E. subrotunda*, or *E. meleagridis*.

It will be apparent to a skilled person that while a particular *Eimeria* for the invention may currently be assigned to a specific species and genus, that is a taxonomic classification that could change in time as new insights can lead to reclassification into a new or different taxonomic group. However, as this does not change the micro-organism itself, or its antigenic repertoire, but only its scientific name or classification, such re-classified micro-organisms remain within the scope of the invention.

*Eimeria* parasites for use in the invention can be obtained from a variety of sources, e.g. as field isolate from a poultry house, or from various laboratories, (depository) institutions or (veterinary) universities.

A "pharmaceutically acceptable carrier" is an aqueous liquid of a high grade of purity and preferably sterile, for example: water, a physiological salt solution, or a phosphate buffered saline solution. The carrier can comprise further excipients such as stabilisers or preservatives.

A "Xanthan gum" is a well-known high molecular weight polysaccharide, CAS nr. 11138-66-2, and is generally available commercially, in several qualities and purities, for example as Keltrol™, Xantural™, or Kelzan™, from CP Kelco. Details and properties of Xanthan gum are described for example in the 'Xanthan book', $8^{th}$ed., 2008, cpkelco-.com.

For the invention, "about" indicates that a number can vary between ±25% around its indicated value.

For the invention, '% w/v' refers to a percentage in weight per volume. For this aspect of the invention, that refers to the volume of the composition according to the invention.

A "TLR3 agonist" is any compound or substance that can activate a TLR3 (toll like receptor, type 3), i.e. that can induce a signalling event mediated by a TLR signal transduction pathway. In this sense the agonist can be a binding moiety or ligand binding directly to the TLR3, alternatively the activation can be indirect, through the generation of an endogenous or exogenous ligand.

The TLR3 molecule, as well as its activation and the resulting cellular cascade, have all been described in the art. TLR3 agonists are for example: naturally-occurring double-stranded RNA (dsRNA); synthetic ds RNA; and synthetic dsRNA analogue (see, e.g., Alexopoulou et al., 2001, Nature vol. 413, p. 732-738). A suitable TLR3 agonist can activate TLR3 in a selective way, in that it does not substantially activate any other TLR.

Examples of suitable TLR3 agonists for the invention are synthetic ds RNA analogue such as poly I:C, and poly A:U, or variants such as: poly I:C12U. The synthetic ds RNA analogue may have a modified backbone such as by: phosphorothioate modification, halogenation, alkylation (e.g., ethyl- or methyl-modifications), and/or phosphodiester modification.

In the art alternate notations are also being used to describe these analogues; for example poly I:C is also written as: poly I-C; poly-IC; polyI-polyC; poly I:poly C, etc. All these are within the scope of the invention.

As described, the Xanthan gum allows the vaccine that can be prepared from the composition according to the invention, to be administered effectively by a method of mass vaccination, such as by spray. An example is a gel-based spray vaccine as described in EP 15203012. For preparing such a vaccine, the amount of Xanthan gum in the composition will be dependent on the ratio in which the composition will be used to prepare the intended vaccine.

A gel-based spray vaccine as described in EP 15203012 comprises Xanthan gum in an amount of between about 0.3 and about 1.5% w/v Xanthan gum, whereby the % w/v in this case indicates a percentage in weight per volume of the vaccine.

An upper limit for the amount of Xanthan gum that can still be conveniently processed is at about 5% w/v. To allow for a dilution of the composition according to the invention up to a factor of about 4, therefore the composition can comprise between 0.3 and 5% w/v (of the composition) Xanthan gum.

Preferably the composition according to the invention is to be used almost substantially for the preparation of a gel-based spray vaccine such as described in EP 15203012. In that case the composition itself comprises between about 0.3 and about 1.5% w/v (of the composition) Xanthan gum.

Therefore in an embodiment of a composition according to the invention, the composition comprises between about 0.3 and about 1.5% w/v Xanthan gum.

In an embodiment the composition according to the invention comprises 0.4-1.2% w/v (of the composition) Xanthan gum. Preferably the composition comprises 0.5-1% w/v Xanthan gum, 0.5-0.9% w/v, 0.5-0.8% w/v, or even 0.5-0.7% w/v Xanthan gum, in that order of preference.

In an embodiment, the composition according to the invention comprises about 0.6% w/v (of the composition) Xanthan gum.

Preferably "about" means±20% around its value, more preferably "about" means±15, 12, 10, 8, 6, 5, 4, 3, 2% around its value, or even "about" means±1% around its value, in that order of preference.

In comparative experiments, the inventors have found that in a vaccine prepared from the composition according to the invention, poly A:U was more effective in poultry, and specifically in chickens, in stimulating the intestinal immunity against *Eimeria*, than poly I:C was.

Therefore in an embodiment of the composition according to the invention, the TLR3 agonist is poly A:U.

Synthetic dsRNA analogues such as poly I:C or poly A:U are commercially available from suppliers of fine chemicals, for example as a lyophilised sodium salt from Sigma-Aldrich, CAS nr. 24936-38-7.

The amount of the TLR3 agonist to be used in the composition according to the invention is determined with respect to the ratio in which the composition is to be used for the preparation of a vaccine for poultry against Coccidiosis as described herein, and the amount of vaccine to be applied per target poultry.

As the skilled person will appreciate, the composition according to the invention, or parts thereof, may be produced, marketed, or stored in a more concentrated form, e.g. concentrated 2, 3, or more times. The concentrate is then diluted before further use, such as for the manufacture of a vaccine for poultry against Coccidiosis as described herein. In those circumstances the composition may comprise higher amounts of the TLR3 agonist, to arrive at the preferred amount of TLR3 agonist in the resulting vaccine.

A skilled person is perfectly capable of optimising these amounts e.g. over protection against challenge based on gut lesion score.

Preferably the composition according to the invention comprises between about 5 and about 1000 micrograms of TLR3 agonist per millilitre.

This range allows for a dilution of the composition into the vaccine up to a factor of 4, to reach an amount of TLR3 agonist in the vaccine of between about 5 and about 250 of TLR3 agonist per millilitre of the vaccine. When the vaccine is administered at about 0.2 ml vaccine per bird, this delivers between about 1 and about 50 micrograms TLR3 agonist per animal dose.

Therefore in an embodiment of the composition according to the invention, the TLR3 agonist is present in an amount of between about 5 and about 1000 micrograms per millilitre of the composition.

Preferably the composition according to the invention is used almost substantially for the preparation of a vaccine for poultry against Coccidiosis. In that case the composition itself comprises between about 5 and about 250 micrograms of TLR3 agonist per millilitre of the composition.

The terms 'almost substantially' refers to the situation where there are none or only minor further volumes of additions to be made in the preparation of the vaccine from the composition according to the invention; e.g. less than 10% of the volume of the vaccine.

Therefore in a preferred embodiment, the composition according to the invention comprises 5-250 micrograms of TLR3 agonist per millilitre of the composition.

The oocysts for use in the invention can be produced at industrial scale in donor poultry animals, by isolation from their droppings by well-known techniques such as salt flotation, followed by sporulation and sterilisation, and finally counting by light microscopy. Sporulation can be performed e.g. using potassium-dichromate, and sterilisation can be done using sodium-hypochlorite or beta-propio-lactone. All this is well-known in the art.

The sporulation ensures a rapid establishment of a protective infection in the poultry intestine.

Therefore in an embodiment of the composition according to the invention, the live *Eimeria* oocysts are sporulated oocysts.

To induce an effective level of intestinal immunity, the *Eimeria* oocysts selected for use in the vaccine that can be prepared from the composition according to the invention, can be of a particular level of virulence, such as being wild-type or attenuated. For the invention, 'virulence' refers to the aspects of an *Eimeria* that determine its pathology, mainly its rate of replication, level of damage done to the intestines of an infected bird, effect on growth rate, and level of excretion an spread through the population. All these can be assessed using well-known methods and parameters, such as gut lesion score, live bodyweight gain, and oocyst output numbers.

Lesion scoring is preferably done as described in European Pharmacopoeia monograph 2326. In short: at necropsy, a score is assigned to symptoms of Coccidiosis in the gut, whereby a score of 0 means no gross lesions, and scores of 1-4 mean increasing severity of thickening of the intestinal wall, increased amounts of blood, and decreased amounts of normal faeces. At a lesion score of 4 there may have been cases of mortality.

The skilled person can assess when to apply *Eimeria* of which type of virulence; for example in conditions of high field infection pressure, an *Eimeria* strain of higher virulence such as a wildtype strain may be advantageous in the vaccine produced from the composition according to the invention, instead of an attenuated strain.

Therefore, in an embodiment of the composition according to the invention, at least one of the live *Eimeria* oocysts is from an attenuated strain of *Eimeria*.

"attenuated *Eimeria*" are defined as causing less intestinal lesions, and/or producing a lower oocyst output in the faeces of vaccinated animals, as compared to *Eimeria* of the same species that are of higher virulence; for example at least 10% less gut lesion score, and/or lower oocyst output; more preferably at least 20%, 30%, 40%, or even at least 50% less gut lesion score, and/or lower oocyst output, in that order of preference.

Attenuation of *Eimeria* can be obtained in vitro, for instance by passageing through experimental animals and selection, or via recombinant DNA technology, all well-known in the art.

One form of attenuated *Eimeria*, are *Eimeria* that are precocious.

Therefore in a preferred embodiment of the composition according to the invention, at least one of the attenuated *Eimeria* is precocious.

*Eimeria* strains that are "precocious" are strains that-compared to their wildtype counterpart-complete their full life-cycle in a target animal with a lesser number of rounds of asexual replication. For example 3 or 4 rounds instead of the normal 4 or 5 rounds for a wildtype strain of the same species. This provides them with an attenuated virulence.

In an embodiment of the composition according to the invention, at least one of the live *Eimeria* oocysts is from a wildtype strain of *Eimeria*.

For the invention "wildtype" refers to an *Eimeria* that has not been attenuated in vitro and that is not precocious. Wildtype strains can e.g. be isolated from infected poultry in nature or from poultry houses not vaccinated against *Eimeria*.

In a preferred embodiment, the composition according to the invention comprises live *Eimeria* oocysts that are attenuated and live *Eimeria* oocysts that are of wildtype virulence.

The composition according to the invention will contain oocysts of at least one species of *Eimeria*. Preferably the composition will comprise *Eimeria* oocysts of more than one species to allow the manufacture of a vaccine providing broad immune protection. Further, the composition can comprise more than one strain of a particular *Eimeria* species, to provide even broader immune-protection.

In an embodiment of the composition according to the invention, the composition comprises live *Eimeria* oocysts of more than one species.

In a preferred embodiment of the composition according to the invention, the composition comprises live *Eimeria* oocysts of more than one strain from the same species.

In a preferred embodiment of the composition according to the invention, the composition comprises live *Eimeria* oocysts of more than one species, and the oocysts from at least one of those species comprise live *Eimeria* oocysts of more than one strain from that species.

In a preferred embodiment of the composition according to the invention, the composition comprises live *Eimeria* oocysts of more than one strain from the same species, whereby at least one of those strains is attenuated, and at least one of those strains is of wildtype virulence.

In an embodiment of a composition according to the invention, the live *Eimeria* oocysts are one or more selected from the group consisting of: *E. tenella, E. acervulina, E. maxima, E. mitis, E. necatrix, E. brunetti, E. praecox, E. mivati, E, hagani, E. meleagrimitis* 1, *E. meleagrimitis* 2, *E. adenoeides, E. gallopavonis*, and *E. dispersa*.

These different species of *Eimeria* can be identified and differentiated in a number of ways well-known in the art. A classical method is by assessing size and appearance of their oocysts by light-microscopy. Alternatives are e.g. classification by serologic markers, or by PCR. Also, when tested in vivo, the different *Eimeria* species characteristically colonise different regions of the avian intestinal tract.

In a preferred embodiment the composition according to the invention comprises live oocysts from the same *Eimeria* species as are present in an existing commercial live *Eimeria* oocyst vaccine. More preferred: the same species and strains of oocysts as in one or more of the commercial *Eimeria* vaccines: Coccivac, Paracox, and Fortegra.

In a preferred embodiment of the composition according to the invention the live *Eimeria* oocysts are from 4 *Eimeria* species: *E. acervulina, E. maxima, E. mitis*, and *E. tenella*, whereby there are 2 strains of *E. maxima*.

In a preferred embodiment of the composition according to the invention the live *Eimeria* oocysts are from 4 *Eimeria* species: *E. acervulina, E. maxima, E. mivati*, and *E. tenella*, whereby there are 2 strains of *E. maxima*.

In a preferred embodiment of the composition according to the invention the live *Eimeria* oocysts are from 7 *Eimeria* species: *E. acervulina, E. brunetti, E. maxima, E. mitis, E. necatrix, E. praecox*, and *E. tenella*, whereby there are 2 strains of *E. maxima*

In a preferred embodiment of the composition according to the invention the live *Eimeria* oocysts are from 6 *Eimeria* species: *E. acervulina, E. brunetti, E. maxima, E. mivati, E. necatrix* and *E. tenella*.

In a preferred embodiment of the composition according to the invention the live *Eimeria* oocysts are from 5 *Eimeria* species: *E. adenoeides, E. dispersa, E. gallopavonis, E. meleagrimitis* 1, and *E. meleagrimitis* 2.

The amount of live *Eimeria* oocysts to be used in the composition according to the invention, can readily be determined by a person skilled in the art, based on: the ratio in which the composition is to be comprised in the vaccine for poultry against Coccidiosis; the volume of the vaccine per target poultry; and the desired vaccination efficacy.

An indication can be the numbers of live *Eimeria* oocysts that are being used in commercial vaccines which have been available for a long time. Typically the number of oocysts used differs for each of the species of *Eimeria*. For example, Paracox 5 contains per animal dose: about 500 oocysts of *E. acervulina*, about 100 and about 200 oocysts of two strains of *E. maxima* respectively, about 1000 oocysts of *E. mitis*, and about 500 oocysts of *E. tenella*.

In the preparation of a composition according to the invention, its various ingredients can be combined in an order that is convenient for example in view of manufacturing efficiency. For example it may be advantageous to sterilise certain solutions that are used as components of the composition; of course such solutions would at that time not yet comprise the live oocysts.

Such sterilisation can be performed in different ways, e.g. chemically, e.g. using beta-propriolactone; or physically, e.g. by irradiation, or micro-filtration. However, when the sterilisation of a solution comprising Xanthan gum is to be performed by heating, then it is necessary to stabilise the Xanthan gum by the addition of an amount of a metal salt. Without the salt, a heat treatment will destroy the capacity of the Xanthan gum to provide a desired viscosity.

As described in EP 15203012, the amount of the salt is limited in two ways: at the lower side it is limited to about 0.1% w/v (of the composition) metal salt, which is the minimal amount required to stabilise the minimal amount of Xanthan gum. At the upper side the amount of salt is limited to about 0.4% w/v (of the vaccine), by the palatability of the intended vaccine to be prepared from the composition according to the invention. In this case taste is relevant because the target poultry should be willing to ingest the vaccine.

Effectively this means, when combining these limits, and allowing for a dilution of the composition according to the invention by up to a factor of 4, then the composition may comprise between about 0.1 and about 1.6% w/v (of the composition) of a metal salt.

Therefore in an embodiment of a composition according to the invention, the composition comprises between about 0.1 and about 1.6% w/v of a metal salt.

Preferably the composition according to the invention comprises 0.1-1.2% w/v of a metal salt, more preferably 0.1-0.8%, or even 0.1-0.4% w/v (of the composition) of a metal salt, in that order of preference.

This way, parts of the composition according to the invention comprising Xanthan gum may be heat sterilised without damage to the viscosity-modifying properties of the gum. For the invention, a "heat sterilisation" involves an incubation for at least 15 minutes at at least 100° C.

The metal salt in principle can be any metal salt, but preferably the metal salt is a salt from a mono- or bi-valent metal cation. More preferred the cation is an alkali-metal.

The anion of the metal salt is preferably a halogen, sulphate, phosphate, nitrate, or acetate. More preferred a chloride.

Even more preferred, the metal salt is a halogen salt of an alkali-metal; even more preferably of sodium or potassium; even more preferably the metal salt is a sodium-chloride, or a potassium-chloride. Therefore in an embodiment of a composition according to the invention, the metal salt is sodium-chloride, or potassium-chloride.

In order to stimulate the ingestion of the vaccine to be prepared from the composition according to the invention, a colorant can be added. This will appeal at the birds' natural tendency to peck at and ingest such brightly coloured droplets. Consequently, the colorant can be included into the composition according to the invention. Of course the colorant should not negatively interfere with other components of the composition according to the invention, specifically: the viability or stability of the live oocysts. Also the colorant should be pharmaceutically acceptable as ingredient of a vaccine.

Therefore in an embodiment of a composition according to the invention, the composition comprises a pharmaceutically acceptable colorant.

Examples of a "pharmaceutically acceptable colorant" are: for example green (e.g. chlorophyll, E140), red (e.g. carmine, E120), or blue (e.g. Brilliant blue, FD&C Blue No. 1, E133). All are readily available commercially.

The colorant is present in the composition according to the invention in an amount that is suitable to provide a colour to the vaccine prepared from that composition, with an appropriate intensity. Allowing for a dilution of the composition according to the invention up to a factor of 4, the composition comprises between about 0.05 and about 4% w/v (of the composition) colorant.

A red (carmine) colorant proved to be highly effective in stimulating the uptake of a gel-based spray vaccine for poultry comprising Eimeria oocysts.

Therefore in an embodiment of a composition according to the invention, the pharmaceutically acceptable colorant is carmine.

In a preferred embodiment the carmine is present in the composition according to the invention in an amount of 0.1-0.2% w/v (of the composition).

In an embodiment of the composition according to the invention, one or more or all of the conditions apply selected from the group consisting of:
the composition comprises between about 0.3 and about 1.5% w/v (of the composition) Xanthan gum; preferably the composition comprises about 0.6% w/v Xanthan gum;
the TLR3 agonist is poly I:C or poly A:U, preferably poly A:U;
the TLR3 agonist is present in an amount of between 5 and 1000 micrograms per millilitre of the composition; preferably the composition comprises 5-250 micrograms of TLR3 agonist per millilitre;
the live Eimeria oocysts are sporulated oocysts;
the live Eimeria oocysts are from an attenuated strain of Eimeria, preferably the attenuated Eimeria are precocious;
the live Eimeria oocysts are from a wildtype strain of Eimeria;
the composition comprises live Eimeria oocysts of more than one strain from the same species;
the live Eimeria oocysts are one or more selected from the group consisting of: E. tenella, E. acervulina, E. maxima, E. mitis, E. necatrix, E. brunetti, E. praecox, E. mivati, E, hagani, E. meleagrimitis 1, E. meleagrimitis 2, E. adenoeides, E. gallopavonis, and E. dispersa;
the composition comprises live Eimeria oocysts of more than one species, and at least one of those species comprises live Eimeria oocysts of more than one strain from that species;
preferably whereby at least one of those strains is attenuated, and at least one of those strains is wildtype;
the composition comprises between about 0.1 and about 1.6% w/v (of the composition) of a metal salt; preferably the composition comprises between about 0.1 and about 0.4% w/v of a metal salt;
the metal salt is sodium-chloride, or potassium-chloride;
the composition comprises a pharmaceutically acceptable colorant; preferably the pharmaceutically acceptable colorant is carmine; and
the pharmaceutically acceptable colorant is present in the composition in an amount of between 0.05 and 4% w/v (of the composition).

In a preferred embodiment of the composition according to the invention, the TLR3 agonist is poly A:U; the TLR3 agonist is present in an amount of 5-1000 micrograms per millilitre of the composition; the live Eimeria oocysts are sporulated oocysts; the oocysts are E. acervulina, E. maxima, E. mitis and E. tenella; the oocysts of E. maxima are from two strains; the composition comprises between about 0.1 and about 1.6% w/v (of the composition) of a metal salt; the metal salt is sodium-chloride or potassium-chloride; the composition comprises a pharmaceutically acceptable colorant in an amount of 0.05-4% w/v (of the composition); and the pharmaceutically acceptable colorant is carmine.

By applying the various options and preferences as described herein above, a skilled person is able to prepare a composition according to the invention.

Therefore in a further aspect the invention relates to a method for the preparation of a composition according to the invention, the method comprising the admixing of live Eimeria oocysts and a pharmaceutically acceptable carrier, with a TLR3 agonist.

Methods to perform such admixing are well-known in the art, and can be applied at any scale that is convenient or feasible. For example, when the TLR3 agonist was obtained as a powder, this can be dissolved directly into a solution containing live Eimeria oocysts and a pharmaceutically acceptable carrier. Alternatively the TLR3 agonist can be in a solution of itself which can then be added in liquid form.

As described, the composition according to the invention can be used for the preparation of a vaccine for poultry against Coccidiosis that is more efficacious than conventional live Eimeria oocyst vaccines.

Therefore in a further aspect, the invention relates to the use of a composition according to the invention for the manufacture of a vaccine for poultry against Coccidiosis.

Details and preferences of a vaccine for poultry against Coccidiosis for the invention will be described herein below.

The "manufacture" of a vaccine for poultry against Coccidiosis, according to the use according to the invention, can be done using methods well-known and readily applicable by a person skilled in the art. For example, a composition according to the invention, comprising live *Eimeria* oocysts and a pharmaceutically acceptable carrier and a TLR3 agonist are admixed, optionally further excipients can be added, and the resulting vaccine is apportioned into appropriate sized containers and packaged.

The various stages of the manufacturing process are monitored by adequate tests, for instance by immunological tests for the quality and quantity of the oocysts or any other added antigens; by microbiological tests for sterility (excluding of course the live oocysts) and absence of extraneous agents; by tests for biological- and chemical stability; and ultimately by in vitro or in vivo experiments to determine vaccine efficacy and -safety. All these are well known to a skilled person, and are prescribed in Governmental regulations such as the Pharmacopoeia, and in handbooks such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

The manufacture of a vaccine for poultry against Coccidiosis also comprises embodiments wherein the composition according to the invention, or parts thereof, are used in a more or less concentrated form. For example the oocysts may be prepared and stored before use in a form wherein the *Eimeria* oocysts are in much higher numbers than they are intended to be in the vaccine to be prepared therefrom. Also, other parts of the composition may be prepared and stored in concentrated form, such as a solution comprising the Xanthan gum, the metal salt, and/or the colorant. Either one of these can be used as diluent for either one of the others, in any way as will be convenient during the manufacturing process. The skilled person is perfectly capable to calculate the dilution factor to be applied to arrive at a desired final amount or concentration of an active or an excipient in the resulting vaccine.

As described, the vaccine that can be prepared using the composition according to the invention is more efficacious than conventional live *Eimeria* oocyst vaccines. This is achieved by the addition of a TLR3 agonist.

Therefore, in a further aspect the invention relates to a composition according to the invention, for use as a vaccine for poultry against Coccidiosis.

Also, in a further aspect the invention relates to a vaccine for poultry against Coccidiosis, the vaccine comprising a composition according to the invention.

A "vaccine" is well known to be a composition that has a medical effect. A vaccine comprises an immunologically active component, and a pharmaceutically acceptable carrier. The 'immunologically active component', is one or more antigenic molecule(s), here: live *Eimeria* oocysts that are recognised by the immune system of a target poultry, and induce a protective immunological response. The response may originate from the targets' innate- and/or from the acquired immune system, and may be of the cellular- and/or of the humoral type.

A vaccine generally is efficacious in reducing the level or the extent of an infection, for example by reducing the parasitic load, or shortening the duration of the parasite's replication in a host animal.

Also, or possibly as a results thereof, a vaccine generally is effective in reducing or ameliorating the (clinical) symptoms of disease that may be caused by such infection or replication, or by the animal's response to that infection or replication.

The effect of a vaccine against Coccidiosis according to the invention is the prevention or reduction in poultry of an infection by an *Eimeria*, and/or of one or more signs of Coccidial disease that are associated with such infection or replication. Here such (clinical) signs are: gut lesion score, live bodyweight gain, and oocyst output.

A Coccidiosis vaccine like this, may colloquially also be referred to as a vaccine 'against' *Eimeria* or 'against' Coccidiosis, or as an '*Eimeria* vaccine'.

Details and preferences of a Coccidiosis vaccine according to the invention will be described herein below.

"poultry" refers to avians of agricultural relevance, such as: chicken, turkey, duck, goose, partridge, peacock, quail, pigeon, pheasant, guinea fowl, or ostrich. Preferably poultry are chicken, turkey, duck, or goose. More preferably the poultry are chicken or turkey. Most preferred the poultry are chicken.

The target poultry can be of any type such as layers, breeders, broilers, combination breeds, or parental lines of any of such breeds. Preferred poultry type is broilers.

"Coccidiosis" is well known as an intestinal disease-complex caused by coccidial parasites, such as *Eimeria*.

In an embodiment the vaccine for poultry against Coccidiosis according to the invention comprises between about 5 and about 250 micrograms of TLR3 agonist per millilitre of the vaccine.

The vaccine for poultry against Coccidiosis according to the invention may be provided in a form comprising any of the embodiments (preferred or not) as described herein for the composition according to the invention, or any combination of two or more of those embodiments of the composition according to the invention.

The vaccine for poultry against Coccidiosis according to the invention is most efficacious when applied as a gel-based spray vaccine as described in EP 15203012. Therefore the vaccine comprises Xanthan gum, which helps to form droplets that are more readily ingested, and which also helps in the delivery of the TLR3 agonist to the birds' intestines.

The preferred size of the gel-droplets formed when spraying the vaccine according to the invention, is between about 1 and about 4 mm in diameter. To reach that, the vaccine needs to have a relatively high viscosity of between about 200 and about 4000 mPa·s. This viscosity can be achieved by comprising in the vaccine according to the invention Xanthan gum in an amount of between about 0.3 and about 1.5% w/v; whereby the "w/v" in this case refers to the volume of the vaccine.

Therefore, in an embodiment of a vaccine for poultry against Coccidiosis according to the invention, the vaccine comprises 0.3-1.5% w/v Xanthan gum, and has a viscosity of between 200-4000 mPa·s.

"viscosity" for the invention is to be determined using the rotating spindle technique, whereby a sample is measured when equilibrated at a constant temperature. Specifically: viscosity measurements are performed with a Brookfield™ rotational viscometer according to the manufacturer's instructions. The measurement uses an LV4 type spindle, rotating at 100 rpm, and the sample is equilibrated at 25° C. in a water bath.

In an embodiment the vaccine for poultry against Coccidiosis according to the invention is an oral vaccine.

The term "oral" refers to a way of ingestion via the oral cavity. For the invention this refers to the birds pecking up gel-droplets of the vaccine and swallowing those.

As described above, the vaccine according to the invention can be manufactured from the composition according to the invention in different ways, including the sterilisation of parts of the composition comprising Xanthan gum. Such sterilisation can be achieved in different ways; in the case that a solution containing Xanthan gum is to be sterilised by heating, then the Xanthan gum needs to be protected by the addition of a metal salt. As also described herein, there are upper- and lower limits to the amount of metal salt to be used.

Consequently, when a vaccine according to the invention was prepared from a solution of Xanthan gum that was sterilised by heating, then the vaccine will contain between about 0.1 and about 0.4% w/v (of the vaccine) of a metal salt.

Therefore, in an embodiment of a vaccine for poultry against Coccidiosis according to the invention, the vaccine comprises 0.1-0.4% w/v metal salt.

Preferably the metal salt is sodium-chloride or potassium-chloride.

In the vaccine for poultry against Coccidiosis according to the invention, the exact amount of *Eimeria* oocysts per dose, is not very critical, because the oocysts will readily replicate and colonise the hosts' intestines. The vaccine dose only needs to be sufficient to initiate such a productive infection. A higher inoculum dose hardly shortens the time it takes to reach the optimal colonisation in the host, and very high doses are not attractive for economic reasons. In addition, too high doses of vaccine oocysts may cause some pathology by themselves. Evidently, too low a dose, although perhaps capable of establishing an *Eimeria* infection, may take too much time for a proper onset of immunity.

A preferred inoculum dose is therefore between about 10 and about 1×10^5 sporulated oocysts of a species of *Eimeria* per animal dose, more preferably between 100 and 1×10^4 oocysts per dose, between 100 and 5000, or even between 100 and 1000 oocysts/animal dose, in that order of preference.

As will be apparent to the skilled person, the optimal vaccine dose of live *Eimeria* oocysts will depend e.g. on the target animal species, and on the species and the virulence of the *Eimeria* strain used, and may therefore differ between the various *Eimeria* species in one combination vaccine.

Methods to quantify *Eimeria* oocysts for use in the Coccidiosis vaccine according to the invention are well known in the art.

The volume per animal dose of the vaccine for poultry against Coccidiosis according to the invention, can be optimised according to the intended route of application, e.g. for a spray vaccination the dose may be between about 10 µl and about 1 ml per bird. Preferably the volume of spray vaccine is between 0.1 and 0.5 ml per bird, more preferably between 0.1 and 0.3 ml per bird.

Most preferred, the volume of spray vaccine is about 0.2 ml per bird.

Alternatively the vaccine can be administered by spray onto the feed, or as a liquid to the drinking water. In these cases the dose/bird will can be optimised to the amount of feed eaten, or the amount of water drunk. This is within the capabilities of the skilled artisan.

Finding the optimal volume and dose for the various routes of administration, by determining what is an immunologically effective amount of *Eimeria* oocysts per animal dose of a vaccine for poultry against Coccidiosis according to the invention, is well within the routine capabilities of the skilled artisan. This can e.g. be done by monitoring the immunological response following vaccination or after a challenge infection, e.g. by monitoring the targets' signs of disease and clinical scores, most prominently: gut lesion score. Other criteria can be live bodyweight gain, serological parameters, or re-isolation of the pathogen to determine oocyst output. These results can e.g. be compared to a vaccination-challenge response as seen in mock vaccinated animals.

The age, weight, sex, immunological status, and other parameters of the target poultry for the vaccine for poultry against Coccidiosis according to the invention are not critical, although it is favourable to vaccinate healthy targets, and to vaccinate as early as possible to prevent (the consequences of) an early infection by pathogenic *Eimeria*.

Therefore, the vaccine for poultry against Coccidiosis according to the invention is preferably administered at the day of hatch, i.e. at 1 day old.

When favourable, the poultry may be given a booster vaccination later in life.

As the skilled person will appreciate, the use of medicated feed for poultry that is to receive the vaccine against Coccidiosis according to the invention, is to be applied with care. In the period around the planned vaccination, the birds should not receive feed containing anticoccidial drugs; or at least not receive feed containing anticoccidial drugs for which the *Eimeria* oocysts in the vaccine are sensitive.

It is highly efficient to formulate the vaccine for poultry against Coccidiosis according to the invention as a combination vaccine, because in this way multiple immunologic agents can be administered at once, which reduces the discomfort to the target birds, and reduces labour costs. A combination vaccine based on the vaccine according to the invention, comprises in addition another immunologically active compound. In principle this can be any live or killed micro-organism or part thereof; while maintaining the stability and the replicative capacity of the live *Eimeria* oocysts. Also, the additional immunoactive component(s) must be compatible and effective in a vaccine that is to be ingested.

The additional immunologically active compound may be an antigen, an immune enhancing substance, and/or a vaccine. Alternatively, the vaccine according to the invention, may itself be added to a vaccine.

Methods to prepare such a combination vaccine for the invention are within the routine capabilities of the skilled person.

Therefore, in an embodiment, the vaccine for poultry against Coccidiosis according to the invention is characterised in that the vaccine comprises one or more additional immunoactive component(s).

In an embodiment the vaccine for poultry against Coccidiosis according to the invention is a combination vaccine, comprising at least one additional antigen derived from a micro-organism that is pathogenic to poultry. The additional antigen may be a live, live attenuated, or killed micro-organism, or a part thereof.

Preferably the additional antigen from a micro-organism that is pathogenic to poultry is one or more, selected from the groups consisting of:

Viruses: infectious bronchitis virus (IBV), Newcastle disease virus (NDV), adenovirus, egg drop syndrome virus, infectious bursal disease virus (IBDV) (i.e. Gumboro virus), chicken anaemia virus, avian encephalomyelitis virus, fowl pox virus, turkey rhinotracheitis virus (TRT), duck plague virus (duck viral enteritis), pigeon pox virus, Marek's disease virus (MDV), avian leucosis virus, infectious laryngotracheitis virus (ILTV), avian pneumovirus, avian influenza virus (AIV), and reovirus;

Bacteria: *Escherichia coli*, *Salmonella*, Ornitobacterium rhinotracheale, *Haemophilis paragallinarum*, *Pasteurella multocida*, *Erysipelothrix rhusiopathiae*, Erysipelas, *Mycoplasma*, *Campylobacter*, *Shigella*, and *Clostridium*;

Parasites: *Histomonas*, *Isospora*, *Cryptosporidium*, and *Dermanyssus*; and

Fungi: *Aspergillus*.

More preferred additional antigen is one or more selected from the group consisting of: IBV, NDV, IBDV, ILTV, TRT, AIV, MDV, *Mycoplasma*, and *Salmonella*.

A vaccine for poultry against Coccidiosis according to the invention can advantageously be combined with a pharmaceutical component such as an antibiotic, a hormone, and/or an anti-inflammatory drug.

Even the use of an anti-coccidial compound is possible, provided that the *Eimeria* oocysts in the vaccine are not sensitive to that particular drug.

The vaccine for poultry against Coccidiosis according to the invention may contain one or more components that aid the viability and quality of the live *Eimeria* oocysts for use in the invention, thereby promoting the productive replication and establishment of a colonisation in the intestines of target poultry.

In an embodiment the additive is a stabiliser, to stabilise the quantity and the quality of an *Eimeria* oocyst for the invention during formulation, storage, handling, administration, or ingestion. Also suitable preservatives may be added, such as thimerosal, merthiolate, phenolic compounds, or gentamicin.

A vaccine for poultry against Coccidiosis according to the invention can be used either as a prophylactic- or as a therapeutic treatment, or both, as it interferes both with the establishment and with the progression of an infection by a pathogenic *Eimeria*.

Depending on the circumstances of the administration of the vaccine for poultry against Coccidiosis according to the invention, such as field conditions, or target poultry species, it can be advantageous to further optimise the vaccine. This is well within the capabilities of a skilled person, and generally involves the fine-tuning of the efficacy or the safety of the vaccine. This can be done by selection of the strains of *Eimeria* used, by adapting the vaccine dose, -quantity, -frequency, or the -route, or by adapting or adding other constituents of the vaccine (e.g. stabilisers, carriers, diluents, and the like).

In a preferred embodiment of the vaccine for poultry against Coccidiosis according to the invention, the TLR3 agonist is poly A:U; the TLR3 agonist is present in an amount of 5-250 micrograms per millilitre of the vaccine; the live *Eimeria* oocysts are sporulated oocysts; the oocysts are *E. acervulina*, *E. maxima*, *E. mitis* and *E. tenella*; the oocysts of *E. maxima* are from two strains; the vaccine comprises between about 0.3 and about 1.5% w/v (of the vaccine) Xanthan gum; the vaccine has a viscosity of between about 200 and about 4000 mPa·s; and the composition comprises carmine, in an amount of 0.1-0.2% w/v (of the vaccine).

In a further aspect, the invention relates to a method of vaccination of poultry against Coccidiosis, characterised in that the method comprises administering the vaccine for poultry against Coccidiosis according to the invention to said poultry.

As described, the vaccine for poultry against Coccidiosis according to the invention is preferably administered by a method of mass administration, such that the vaccine is ingested, resulting in an efficacious immunisation against pathogenic *Eimeria*.

The preferred method of mass administration of the vaccine for poultry against Coccidiosis according to the invention, is by way of a spray on the birds. This can be done as a coarse spray using an aqueous medium, whereby the droplets produced are generally of a size over 50 μm in diameter.

Such a coarse spray can for example be applied using a hatchery sprayer when immunising day old chicks in hatching trays, or can be applied e.g. using a back-pack type sprayer when immunising older birds in a floor pen setting. The sprayed vaccine is quickly ingested by the birds from the feathers or the floor.

Therefore in an embodiment of a method of vaccination of poultry against Coccidiosis according to the invention, the method comprises the administration of the vaccine by coarse spray on the poultry and/or on their surroundings.

The indication of the vaccine being sprayed "on the poultry" does not require that all or most of the vaccine reaches the body of the birds. Rather this indicates that no particular part of the body needs to be specifically targeted. When comprising Xanthan gum, the vaccine droplets will become somewhat sticky and when delivered as a coarse spray tend to adhere to some extend to the birds' feathers. However, a part of the vaccine will not land on, or stay on, the body of the birds, but will end up on the floor or on the bottom of a container in which the birds are kept. This is fine, as the birds will quickly start to peck at such droplets and ingest them.

In a preferred embodiment of a method of vaccination of poultry against Coccidiosis according to the invention by coarse spray, the vaccine droplets are of a size between about 1 and about 4 mm in diameter.

Standard spray vaccination equipment can be used, and by selecting the proper conditions, such as the nozzle and the pressure used, a skilled person can conveniently arrive at droplets of such sizes. Because of the pseudoplastic properties of Xanthan gum, no increased pressurisation, or use of special high-pressure spray nipples are required.

The administration regime for the vaccination according to the method of the invention to a target poultry, can be in single or in multiple doses, in a manner compatible with the formulation of the vaccine and with practical aspects of the animal husbandry.

Preferably, the regime for a method of vaccination of poultry against Coccidiosis according to the invention is integrated into existing vaccination schedules of other vaccines that the target poultry may receive, in order to reduce stress to the animals and to reduce labour costs. These other vaccines can be administered in a simultaneous, concurrent, or sequential fashion, in a manner compatible with their registered use.

Therefore in an embodiment of a method of vaccination of poultry against Coccidiosis according to the invention, the vaccine is administered in a combination with another poultry vaccine.

These methods of vaccination of poultry against Coccidiosis according to the invention are very effective in protecting poultry against infection with *Eimeria*, and/or against (clinical) signs of disease associated with such an infection. In particular this prevents suffering and discomfort the poultry, and prevents significant economic damage to commercial poultry operations.

Therefore, in a further aspect the invention relates to a method for the reduction of an infection with *Eimeria* in poultry, or of associated signs of disease, characterised in that the method comprises administering to said poultry a vaccine for poultry against Coccidiosis according to the invention.

In view of the surprising effect of the protection of an analogue of dsRNA by combining it with Xanthan gum, such that it can now be administered by oral route, in relatively low concentrations, and still induce in the avian gut, to yield a detectable clinical improvement on the protective response obtained following oral *Eimeria* vaccination of poultry, the invention relates to a method for the protection of a TLR3 agonist during oral delivery.

Therefore, in a further aspect, the invention relates to a method for the delivery of a TLR3 agonist to the avian gut by oral route, characterised in that the TLR3 agonist is admixed with a Xanthan gum.

The TLR3 agonist can itself have a pharmaceutical effect, and/or can function (also) in adjuvating the immunological- or pharmaceutical effect of another compound.

Preferably the Xanthan gum for admixing with the TLR3 agonist is as described in one or more of the aspects and their various embodiments and preferences, as described herein.

The invention will now be further described by the following, non-limiting, examples.

EXAMPLES

1. Effect of TLR3 Agonist on *Eimeria* Vaccine Efficacy; Earlier Onset of Immunity 1.1. Experimental Outline This experiment tested the effect on the onset of immunity of Paracox™ 8 vaccine by the addition of a TLR3 agonist. A dose titration was performed for the TLR3 agonist. Results were directly compared with birds vaccinated with Paracox 8 only.

Two hundred and ten one day-old birds were divided into seven groups of 30 birds. All birds in groups 1-5 were vaccinated with Paracox vaccine, diluted in 0.6% Xanthan Gum, containing 0.1% carmine; by oral gavage of 0.5 ml vaccine. Groups 1-4 each received a different amount of TLR3 agonist. The birds in group 5 were vaccinated with Paracox 8 only and the birds in groups 6 and 7 were not vaccinated (see Table 1). All birds were kept in their groups in separate pens for 14 days post vaccination (PV). Faecal samples were collected on days 7, 14 and 19 from the control birds (Groups 6 and 7) to monitor for a Coccidiosis infection. On day 13 PV prior to challenge, all birds were uniquely identified by numbered tag, then on day 14 PV each bird in groups 1-6 was challenged with 15.000 oocysts of *E. tenella* wildtype. While this date of challenge was too early for normal Paracox vaccination to reach full protection, it allowed the detection of any enhancement in onset of immunity.

On day 5 post challenge all the challenged birds, and those in group 7 were euthanized and examined post mortem for lesions associated with an *E. tenella* infection. The birds were observed daily throughout the study for any clinical signs which may have been related to an *Eimeria* spp. infection.

TABLE 1

Schedule of vaccinations and challenges of Example 1

| | Treatment | | |
|---|---|---|---|
| Group | Vaccine | TLR3 agonist (µg/animal dose | Challenge |
| 1 | Yes | 5 | Yes |
| 2 | | 10 | |
| 3 | | 20 | |
| 4 | | 40 | |
| 5 | | 0 | |
| 6 | No | 0 | |
| 7 | | 0 | No |

1.2. Materials & Methods

A commercial batch of Paracox 8 vaccine was used, which was resuspended to give one full dose per 0.5 ml. The vaccine was diluted 1:1 with a 2× concentrated stock of a diluent containing 1.2% Xanthan gum solution, in 75 mM NaCl (i.e. 0.44% w/v), and containing 0.2% w/v Carmine (E 120). The diluent stock had been sterilised by autoclaving at 115° C. for 30 minutes.

The Paracox 8 vaccine dilution was prepared in a safety cabinet. 100 ml of vaccine (containing 200 doses) was prepared for each group; two 1000 dose sachets of the vaccine were shaken and massaged vigorously for 1 minute to ensure resuspension of the oocysts. The contents of the sachets were pooled in a suitable container. For each vaccine 21 ml of the neat pooled Paracox 8 vaccine was added to a sterile glass Duran bottle (appropriately labelled with the group number). A TLR3 agonist stock solution at 10 mg/ml was thawed quickly, and then the appropriate volumes of the agonist and water were added to the vaccine and mixed thoroughly. Next, 50 ml of the 2× diluent stock was added to each Duran bottle (depending on group). All formulations were then thoroughly mixed by shaking for at least 10 minutes prior to use.

In the vaccine samples Groups 1-4 received an amount of the TLR3 agonist stock at 10 mg/ml, to reach the intended amount of agonist; group 1: 100 µl, group 2: 200 µl, etc.; all these volumes were completed with sterile water up to 29 ml.

TLR3 Agonist:

The TLR3 agonist used was poly A:U, double stranded homopolymer (Sigma Aldrich). It was dissolved from a lyophilised sodium salt to a 10 mg/ml stock solution, and stored at −70° C. until use.

Challenge Materials:

The challenge material was a batch of *E. tenella* wildtype, sterile sporulated oocysts, stored at 2-8° C. until use. The concentration of the oocysts in the challenge material was determined using a modified Fuchs-Rosenthal counting chamber. From this a dilution was made to give 15.000 oocysts per 0.5 ml challenge dose.

Test Animals:

Experimental animals were Lohmann SPF chicks of mixed sex, day old at vaccination. Birds were placed randomly into groups of 30, in individual pens.

Birds were marked individually with swift tags on day 13 post vaccination.

The birds were vaccinated by administering 0.5 ml of the appropriate vaccine preparation per bird, by oral gavage.

Chicks were challenged with 0.5 ml each of the *E. tenella* wild type preparation, by oral gavage, all within 1 hour from each other.

Throughout the experiment all birds were observed daily for clinical signs of coccidial infection such as diarrhoea or blood in the faeces, depression or inappetance. No special findings were observed. 3 chicks died from causes unrelated to the experiment: 1 from group 1, and 2 from group 2.

On day 5 post challenge all birds were euthanized, and sent for necropsy. Post mortem, all birds from each group were examined for gut lesions relating to *E. tenella*.

For the purpose of checking vaccine- or challenge take, faecal collections were made from the floor of the pens of the control birds (groups 6 and 7) on days 7, 14 and 19 post vaccination. Each sample was taken from the litter in the pen, the samples were approximately 10-20 grams and were representative of the whole pen e.g. collected from 4 corners and from the middle of the pen; the samples were fresh and contained the minimum amount of litter as was possible. Each sample was double bagged, labelled, and stored at 2-8° C. until processing. The oocysts were detected as per standard practice, and the numbers were calculated using the Modified McMaster counting technique.

1.3. Results

Gut lesion scores relating to *E. tenella* were determined at 5 days post challenge by necropsy. The lesion assessments were carried out blinded with respect to treatment group, with the exception of the control groups 6 and 7. Lesion score results for groups 1-7 are summarised in FIG. 1, panels A through G respectively, as percentage of animal displaying a certain score. Apart from an occasional death, for these groups n=30.

The lesion score results were as expected for the control groups; the unchallenged birds in group 7 all had a lesion score of 0, whereas the unvaccinated, challenged birds of group 6 had high scores of 3 or 4, resembling the lesion score profile of naive birds.

The birds in group 5 (Paracox 8 vaccine only) had scores which were weighted to the higher end of the scoring range. This was not unexpected as the birds were challenged at 14 days post vaccination when this vaccine normally only provides partial protection. However this facilitated observing whether there had been an earlier onset of immunity as result of the addition of the TLR3 agonist.

The birds in groups 1 and 2, which received the low doses of the TLR3 agonist (5 or 10 μg/bird respectively), showed a full range of lesion scores with a clearly increased proportion of lower lesion scores. In groups 3 and 4, where the birds received the higher two dose levels of the TLR3 agonist (20 or 40 μg/bird respectively), the lesion score profile was not very different compared to the birds vaccinated with Paracox 8 only (group 5).

Faecal collections showed that no oocysts were detected in any of the faecal samples taken. This demonstrated that the birds in group 7 remained uninfected throughout the study. For group 6, also no oocysts were detected in the final collection, however this was probably related to the severe illness of these birds as was demonstrated by their gut lesion scores, preventing normal faeces to form.

1.4. Conclusions

Of all the TLR3 agonist amounts tested, the birds receiving the lower doses of 5 or 10 μg per animal, had the best lesion score results, with a bigger range of scores, and a clear tendency towards the lower lesion scores. This is convincing proof of the induction of an earlier onset of immunity.

In this experiment the higher amounts of TLR3 agonist/animal did not present clear immunological enhancement. This may be an indication that there is an optimum profile in the dose-effect of the TLR3 agonist. However, in another vaccination-challenge experiment (Example 2) a higher dose of TLR3 agonist/animal did show a clear benefit compared to a Paracox 8 vaccine only group.

2. Effect of TLR3 Agonist on *Eimeria* Vaccine Efficacy; Earlier Onset of Immunity 2

In an experiment with largely the same setup and procedures as that described in Example 1, amounts of TLR3 agonist of 10 or 20 micrograms/bird were tested for effect on enhancement in onset of immunity.

Groups of 20 chickens were used, which received treatment as displayed in Table 2

TABLE 2

Schedule of vaccinations and challenges of Example 2

| | Treatment | | |
|---|---|---|---|
| Group | Vaccine | TLR3 agonist (μg/animal dose) | Challenge |
| 1 | Yes | 10 | Yes |
| 2 | | 20 | |
| 3 | | 0 | |
| 4 | No | 0 | |
| 5 | | 0 | No |

2.1. Results

Figure 2:
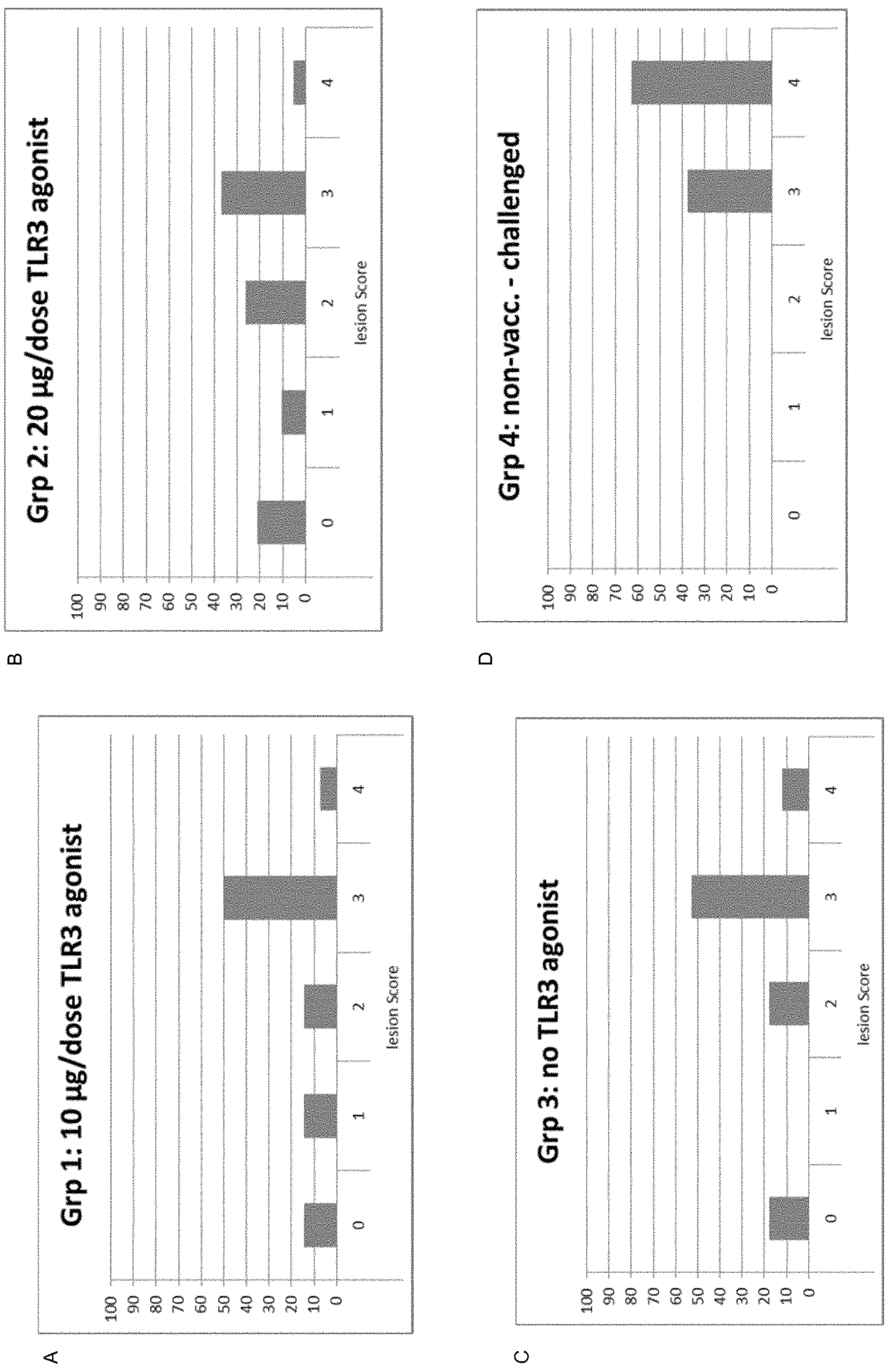
Figure 2:
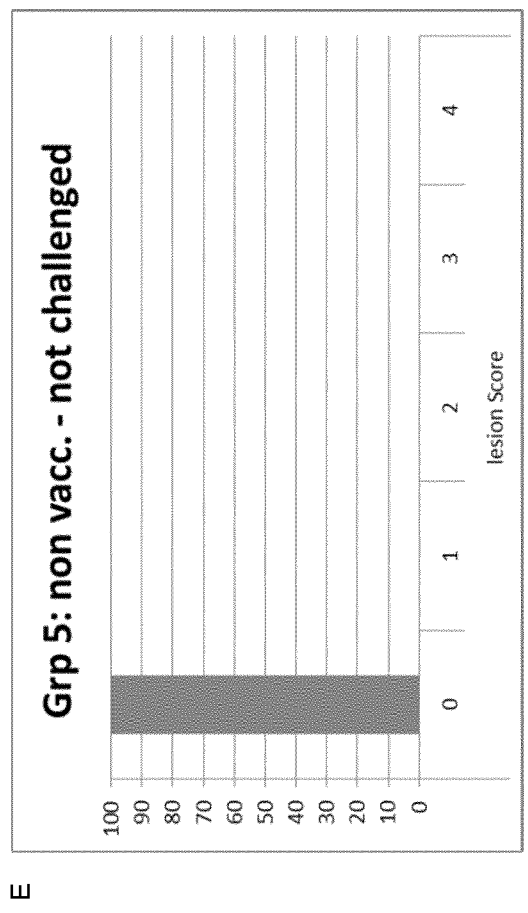

The lesion score results of this experiment are represented in FIG. 2, in panels A through E, for the groups 1-5 respectively.

The results were as expected for the control groups: the unvaccinated—unchallenged birds of group 5 all had a lesion score of 0, whereas the unvaccinated—challenged birds had high scores of 3 or 4, indicating these had no protection against the challenge. Challenge severity appeared to be slightly below that applied in Example 1.

The birds receiving Paracox 8 vaccine only, group 3, had a range of scores, but weighted to the higher end of the scoring range. Like in Example 1 this was to be expected because of the early date of challenge (2 weeks) post vaccination.

The treatment groups 1 and 2, had a broad lesion score profile, with a higher proportion of lower lesion scores, than the birds in vaccine group 3, indicating that the TLR3 agonist did enhance the vaccine's immunity in respect of the onset of immunity it induced.

In this experiment, the higher amount of TLR3 agonist (20 μg/bird) seemed more effective than the lower amount (10 μg/bird) in inducing an earlier onset of immunity.

3. Effect of TLR3 Agonist on *Eimeria* Vaccine Efficacy; Reduction of Oocysts Per Dose A further experiment was performed to test the effect of a TLR3 agonist on the efficacy of live *Eimeria* oocyst vaccination. In this experiment a number of large groups were treated, to assess the effect of the TLR3 agonist on the dose of the vaccine. The set-up and performance in essence was the same as that for the experiments in the Examples 1 and 2, except that: chickens were of commercial layer type; the vaccine used was Paracox™ 5, the dose of TLR3 agonist/bird was fixed at 7.5 μg, the vaccination was administered by coarse spray at 0.2 ml/bird, and the challenge was at day 21 post vaccination and with 4 separate strains.

3.1. Experimental Outline 1125 chicks of day-old were divided over 9 groups of 125 animals; one group remained unvaccinated, the other 8 groups received Paracox 5 vaccine in different dosages, and either with or without TLR3 agonist, see Table 3. Vaccine contained Xanthan gum, and was applied as a coarse spray using a standard hatchery spray applicator.

On day 21 post vaccination, 80 birds from each treatment group were allocated to one of four challenge types, leaving 20 birds per species-challenge subgroup. A total of 720 birds were given a 0.5 ml oral gavage of one of four *Eimeria* species challenges. Five birds from control group 1 were left unchallenged and kept in their original pen for assessment of baseline necropsy assessments on day 28 p.v.

All birds were weighed individually on day 20 p.v. prior to allocation to challenge type, and again on day 28 p.v. prior to necropsies, to determine live bodyweight gain. Bulked faecal samples were collected from day 21 to 25 and from day 25 to 28 p.v. from all pens for oocyst output enumeration. Ten birds per challenge treatment group for *E. acervulina*, *E. maxima* and *E. tenella* challenge types were necropsied for assessment of gut lesions. As *E. mitis* does not produce pathognomonic gut lesions, ten birds from group 1 (controls) that were challenged with *E. mitis* were necropsied for parasite status to confirm uptake of challenge.

3.2. Materials & Methods

Test Animals:

Hyline™ brown, commercial layer chickens. Of male gender, number tagged individually. All chicks were day-old at day of vaccination. Birds were kept in appropriate pens under climatised and controlled conditions, on bedding of wood shavings. Feed was unmedicated.

Chicks were closely monitored throughout the study; 7 birds died in the first week after vaccination of causes unrelated to the treatment, these were from different groups.

TABLE 3

Schedule of vaccinations and challenges of Example 3

| | | Treatment | |
|---|---|---|---|
| Group | Vaccine dose | TLR3 agonist (X µg/bird) | Challenge |
| 1 | none | none | Yes, one of: *E. acervulina*, *E tenella*, *E. mitis*, or *E. maxima* (n = 20) |
| 2 | 1:20 | no | |
| 3 | 1:20 | yes | |
| 4 | 1:10 | no | |
| 5 | 1:10 | yes | |
| 6 | 1:4 | no | |
| 7 | 1:4 | yes | |
| 8 | full | no | |
| 9 | full | yes | |

Vaccines:

Sachets of Paracox 5, at a total of 11.000 doses were shaken thoroughly, divided into the various groups in respective dilutions in water, mixed with TLR3 agonist where intended, and all vaccines were mixed 1:1 with a sterile 2× stock of diluent containing Xanthan gum (1.2%), NaCl (75 mM), and carmine (0.2%), as described.

The amounts of the oocysts in the 'full' dose vaccine for groups 8 and 9 were per dose: *E. acervulina*: 500; *E. maxima*, strain CP: 200; *E. maxima*, strain MFP: 100; *E. mitis*: 1000; and *E. tenella*: 500 oocysts.

The TLR3 agonist used was poly A:U at a dose of 7.5 µg per bird.

Vaccines were administered as a coarse spray, using a Spraycox™ II machine, according to the manufacturer's instructions: volume and pressure settings were calibrated prior to use; vaccines were shaken well before use; vaccines were administered lowest to highest dose, and groups without agonist prior to groups with agonist, with intermediate rinsing. Vaccine volume was set at 20 ml per 100 birds. Once vaccinated, birds were kept in the tray in which they were vaccinated for at least 30 minutes in a well-lit and warm area before transfer to holding pens.

Challenge Materials:

All challenge materials were liquid suspensions of sporulated oocysts from 4 different species: *E. acervulina* (Ea), *E. tenella* (Et), *E. mitis* (Emit), or *E. maxima* (Emax). The intended number of oocysts were determined using a modified Fuchs-Rosenthal counting chamber, as respectively: Ea: $1\times10^6$/bird in 1 ml; Et: $3\times10^4$/bird in 0.5 ml; Emit: $3\times10^5$/bird in 1 ml; Emax: $1\times10^4$/bird in 0.5 ml.

Challenge material was administered individually, by oral gavage.

Necropsy and Lesion Scoring:

Staff performing oocyst counting or lesion scoring were blinded from information on the treatments. Lesion scoring used standard criteria, specific for each of the challenge species (Ea, Et, and Emax).

3.3. Results

Take of Vaccine and Challenge:

Faecal samples of group 1 birds remained negative for oocyst counts prior to challenge indicating that group 1 was coccidia free prior to challenge. Oocyst counts of faecal samples taken from vaccinated groups 2 to 9 were all positive from day 11 p.v., indicating that vaccinal oocyst replication was successful for all vaccinated groups.

Challenge take was also successful with clinical symptoms of Coccidiosis observed from three days post challenge until necropsy. At necropsy on day 28 p.v., birds challenged with *E. acervulina*, *E. maxima* and *E. tenella* had gut lesion scores above 0, and all gut scrapings of control birds challenged with *E. mitis* were positive for oocysts confirming challenge was effective.

Live Bodyweight Gain:

Results of average live bodyweight gains in grams, from day 20 trough day 28 post vaccination, for the different challenge subgroups, are presented in Table 4. Size of the different subgroups was 20 animals.

For *E. acervulina*, all dilutions of vaccine had a significantly better ($p<0.01$) average live bodyweight gain compared with the unvaccinated-challenged control group, with the exception of the 1/20 dilution (group 2), which had a significantly lower average bodyweight gain. However this dramatically recovered in the presence of TLR3 agonist.

Of the birds in the vaccinated subgroups receiving one of the other challenge species (*E. tenella*, *E. mitis*, or *E. maxima*), most had significantly better average live weight gains compared to their unvaccinated-challenged group. However no effect of vaccine dilution or the presence of TLR3 agonist could be detected.

It is assumed that the vaccine doses applied, even in the diluted samples still contained too high doses of oocysts to be able to observe an effect on bodyweight gain. In a repeat experiment higher vaccine dilutions will be used.

TABLE 4

Average live bodyweight gains in grams, from day 20 trough day 28 post vaccination, for the different challenge subgroups (n = 20)

| Group | E. acervulina | E. tenella | E. mitis | E. maxima |
|---|---|---|---|---|
| 1 - unvacc. - no TLR3 agonist | 63.7 | 73.3 | 50.4 | 53.7 |
| 2 - 1/20 dose | 36.7 | 84.0 | 72.3 | 92.3 |
| 3 - 1/20 dose + TLR3 agonist | 88.1 | 84.2 | 73.1 | 90.7 |
| 4 - 1/10 dose | 85.6 | 77.6 | 60.2 | 76.5 |
| 5 - 1/10 dose + TLR3 agonist | 83.5 | 87.4 | 72.6 | no data |
| 6 - 1/4 dose | 88.8 | 91.2 | 70.6 | 83.4 |
| 7 - 1/4 dose + TLR3 agonist | 93.2 | 84.2 | 74.5 | 81.6 |
| 8 - full dose | 85.3 | 84.5 | 71.5 | 86.4 |
| 9 - full dose + TLR3 agonist | 93.0 | 83.0 | 72.0 | 82.6 |

Gut Lesion Scores:

Results of average gut lesion scores by challenge type and treatment group are represented in Table 5. for these groups n=20.

Only 50% of the unvaccinated control birds challenged with E. acervulina had lesion scores over 2.

Vaccinated-challenged birds had no significant difference in the distribution of their lesion scores. Eighty percent of the unvaccinated control birds challenged with E. maxima had lesion scores over 2. There was a significant (p<0.05) difference in the distribution of lesions for all vaccinated birds (groups 2-9) compared to the unvaccinated birds (all p values <0.03), irrespective of vaccine dilution or the presence of TLR3 agonist. Ninety percent of the unvaccinated control birds challenged with E. tenella had lesion scores over 2. Although for the standard vaccine in the absence of TLR3 agonist (group 8) the percentage of birds with lesion scores over 2 was reduced to 60%, the change in the overall distribution was not statistically significant (p=0.07). There was however a significant reduction in the distribution of the lesion scores with vaccine diluted 1/4 (group 6; p=0.001). At higher dilutions of vaccine (1/10, group 2, and 1/20, group 4) 70% of birds had lesion scores over 2, and the distributions were not significantly different from the unvaccinated challenged control group. The presence of TLR3 agonist reduced the percentage of birds with lesion scores over 2 to 20% (group 5, 1/10 dose) and 50% (group 3, 1/20 dose) respectively, resulting in a lesion score distribution that was statistically significantly different from the control group for group 5 (p=0.003), and almost statistically significant for group 3 (p=0.0509).

3.4. Discussion and Conclusions

There were no significant differences in bird bodyweights between control and vaccinated treatment groups for each challenge type on day 20 p.v. Faecal samples from the unvaccinated controls (group 1) confirmed that group 1 remained coccidia free prior to challenge. Oocyst counts from faecal samples taken from vaccinated treatment groups 2-9 were all positive from day 11 p.v. indicating vaccinal oocyst uptake and re-cycling was successful for all vaccinated groups. Recounting of challenge materials used, showed that challenge dose was within ±2% of target.

At necropsy on day 28 p.v., unvaccinated control birds challenged with E. acervulina, E. maxima or E. tenella had gut lesion scores over 2 in 50%, 80% and 90% of the birds respectively. Also all gut scrapings of control birds challenged with E. mitis were positive for oocysts.

Although the lesion scores obtained following challenge with E. acervulina were relatively mild, high levels of oocyst output and a significant effect on weight gain was seen in the unvaccinated control group, thus confirming that all challenges were effective. Vaccine dilution showed a variable effect on efficacy depending upon the challenge species and the parameter being measured. Dilution of vaccine up to 1/20 had no effect on any of the efficacy parameters investigated for either E. maxima or E. mitis, indicating that these antigens are significantly in excess within the Paracox 5 formulation. In contrast, for E. tenella reduced levels of protection in terms of both reduction in oocyst output and lesion score was observed at vaccine dilutions of 1/10 or higher. Similarly for E. acervulina, when vaccine was diluted 1/20, no protection was observed against reduction in weight gain. Gut lesions were too mild to demonstrate a definitive outcome. In all cases where reduced protection was observed due to vaccine dilution, the inclusion of TLR3 agonist in the vaccine formulation was beneficial.

Overall these results prove that the inclusion of a TLR3 agonist in the vaccine formulation may increase vaccine potency at lower antigen doses up to 4 fold, while obtaining the same level of protection against challenge.

TABLE 5

Average gut lesion scores by challenge type and treatment group (n = 20)

| Group | E. acervulina | E. tenella | E. maxima |
|---|---|---|---|
| 1 - unvacc. - no TLR3 agonist | 1.5 | 2.9 | 2.1 |
| 2 - 1/20 dose | 1.5 | 2.2 | 0.9 |
| 3 - 1/20 dose + TLR3 agonist | 0.9 | 1.7 | 1.2 |
| 4 - 1/10 dose | 1.0 | 2.0 | 1.2 |
| 5 - 1/10 dose + TLR3 agonist | 1.3 | 1.0 | 1.0 |
| 6 - 1/4 dose | 1.0 | 0.6 | 0.8 |
| 7 - 1/4 dose + TLR3 agonist | 1.4 | 0.3 | 1.2 |
| 8 - full dose | 1.5 | 2.0 | 0.9 |
| 9 - full dose + TLR3 agonist | 1.1 | 0.2 | 0.9 |

LEGEND TO THE FIGURES

FIG. 1 displays the results of the vaccination-challenge experiment described in Example 1. Panels A through G present the lesion scores after vaccination-challenge treatment for the groups 1-7 respectively.

The horizontal axis presents the lesion score number 0-4, and the vertical axis the percentage of the birds displaying that lesion score in that group. For these groups n=30.

FIG. 2

Results of lesions scores that resulted from the vaccination-challenge experiment of Example 2. Panels A-E depict the results of groups 1-5 respectively. Axes used are the same as in FIG. 1. For these groups n=20.

The invention claimed is:

1. A composition comprising live Eimeria oocysts and a pharmaceutically acceptable carrier, wherein the composition further comprises between about 0.3 and about 5% w/v Xanthan gum and a TLR3 agonist.

2. The composition of claim 1, wherein the TLR3 agonist is poly A:U.

3. The composition of claim 1, wherein the live Eimeria oocysts are sporulated oocysts.

4. The composition of claim 1, wherein the live Eimeria oocysts are selected from the group consisting of: E. tenella, E. acervulina, E. maxima, E. mitis, E. necatrix, E. brunetti, E. praecox, E. mivati, E. hagani, E. meleagrimitis 1, E. meleagrimitis 2, E. adenoeides, E. gallopavonis, E. dispersa, and any combination thereof.

5. The composition of claim 1, wherein the composition further comprises between about 0.1 and about 1.6% w/v of a metal salt.

6. The composition of claim 1, wherein the composition further comprises a pharmaceutically acceptable colorant.

7. A method for the preparation of a composition comprising live *Eimeria* oocysts, a pharmaceutically acceptable carrier, and a TLR3 agonist comprising admixing live *Eimeria* oocysts and a pharmaceutically acceptable carrier, with a TLR3 agonist.

8. The composition of claim 1, comprising 0.3-1.5% w/v Xanthan gum, and having a viscosity of between 200-4000 mPa·s.

9. A method of vaccinating poultry against Coccidiosis, comprising administering the composition of claim 1 to said poultry.

10. The method of vaccinating of claim 9, comprising administering the vaccine by coarse spray onto the poultry and/or onto their surroundings.

11. A method for the reduction of an infection with *Eimeria* in poultry, or of associated signs of disease, comprising administering the composition of claim 1 to said poultry.

12. A method for the delivery of a TLR3 agonist to an avian gut by an oral route, wherein the TLR3 agonist is admixed with a Xanthan gum.

* * * * *